(12) United States Patent
Dandala et al.

(10) Patent No.: US 6,797,831 B2
(45) Date of Patent: Sep. 28, 2004

(54) PROCESS FOR LACTONIZATION TO PRODUCE SIMVASTATIN

(75) Inventors: Ramesh Dandala, Hyderabad (IN); Sonny Sebastian, Hyderabad (IN); Sanapureddy Jagan Mohan Reddy, Cuddapah (IN); Meenakshisunderam Sivakumaran, Hyderabad (IN)

(73) Assignee: Aurobindo Pharma Limited, Hyderabad (IN)

(*) Notice: Subject to any disclaimer, the term of this patent is extended or adjusted under 35 U.S.C. 154(b) by 0 days.

(21) Appl. No.: 10/440,537

(22) Filed: May 19, 2003

(65) Prior Publication Data

US 2004/0019225 A1 Jan. 29, 2004

(51) Int. Cl.[7] ............................................. C07D 309/30
(52) U.S. Cl. ....................................................... 549/292
(58) Field of Search ......................................... 549/292

(56) References Cited

U.S. PATENT DOCUMENTS

| | | | |
|---|---|---|---|
| 4,820,850 A | * 4/1989 | Verhoeven et al. | 549/292 |
| 4,916,239 A | * 4/1990 | Treiber | 549/292 |
| 5,917,058 A | * 6/1999 | Kumar et al. | 549/292 |

* cited by examiner

*Primary Examiner*—Amelia Owens
(74) *Attorney, Agent, or Firm*—Jay R. Akhave

(57) ABSTRACT

There is disclosed a process for the manufacture of simvastatin of Formula I

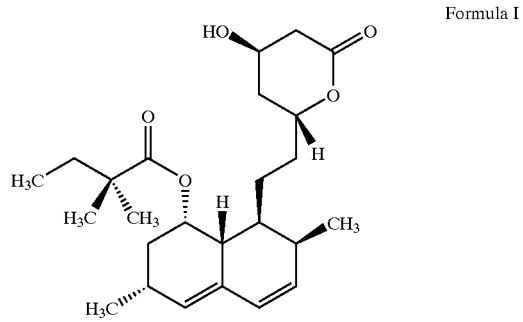

Formula I which comprises heating a compound, namely acid or ammonium salt of compound of Formula II,

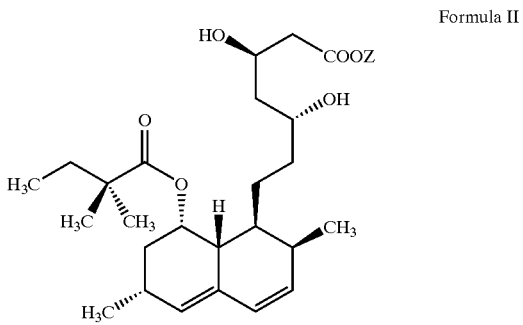

Formula II where Z is H or $NH_4$ in an organic solvent at a temperature of 130–140° C.

8 Claims, No Drawings

PROCESS FOR LACTONIZATION TO PRODUCE SIMVASTATIN

| Name | Residence | Citizenship |
|---|---|---|
| Ramesh Dandala | 403, Janapriya Pramila Enclave Uma Nagar, Kundanbagh, Begumpet Hyderabad - 500 016 (India) | India |
| Sonny Sebastian | 505, Vishal Towers, A Block A.S. Raju Nagar, Kukatpally, Hyderabad - 500 072 (India) | India |
| Sanapureddy Jagan Mohan Reddy | 4/134, Pakeerpalli, Sankarapuram (post) Cuddapah - 516 002 (India) | India |
| Meenakshisunderam Sivakumaran | D-1, Hidden Treasure Apartments Near Ayyappa Swami Temple Lane Somajiguda, Hyderabad - 500 082 (India) | India |

CROSS REFERENCE TO RELATED APPLICATIONS

| | | |
|---|---|---|
| Indian Patent Application | Filing Date | May 18, 2001 |
| | Application No. | 401/MAS/01 |
| | Status | Not issued |
| PCT Application | Filing Date | May 16, 2002 |
| | Application No. | PCT/IN02/00122 |
| | Publication Date | Nov. 28, 2002 |
| | Publication No. | WO 02/094804 A1 |

STATEMENT REGARDING FEDERALLY SPONSORED RESEARCH AND DEVELOPMENT

Not Applicable.

BACKGROUND OF INVENTION

This invention relates to a process for lactonization to produce simvastatin.

Lovastatin, simvastatin, pravastatin, atorvastatin and mevastatin are well known potent antihypercholesterolemic agents that function by limiting cholesterol biosynthesis by inhibiting the enzyme, HMG-CoA reductase. This class of compounds, referred to generally as statins, are produced either by natural fermentation process or through semi-synthetic and totally synthetic means thereof. Two of the most popular compounds in this therapeutic category are simvastatin and atorvastatin. The former is one of the most prescribed drugs in the treatment of primary hypercholesterolemia with minimum side effects and well established safety profile. The use of highly pure simvastatin is exceedingly desirable in preparation of a pharmaceutical form as it would avoid accumulation of impurities during prolonged usage and would reduce the possible side effects during medical treatment.

1. Field of the Invention

A process for lactonization to produce simvastatin of Formula I

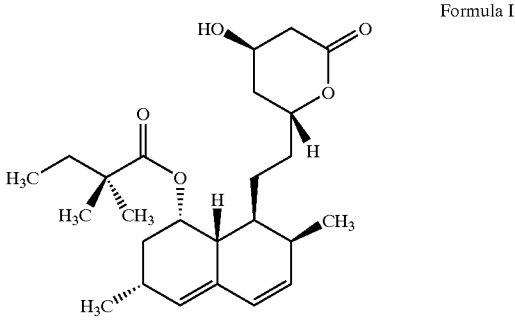

Formula I

2. Description of Related Art

In most of the synthetic methods known to manufacture simvastatin (Formula I) shown below,

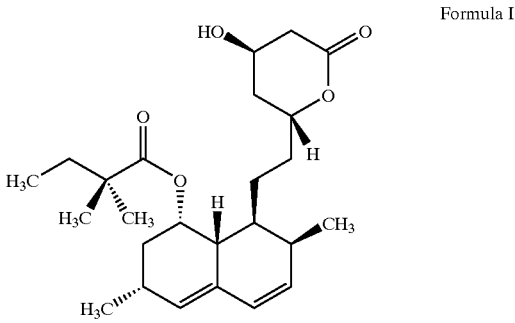

Formula I hydroxyacid ammonium salt (Formula IIA) also shown below is the common intermediate,

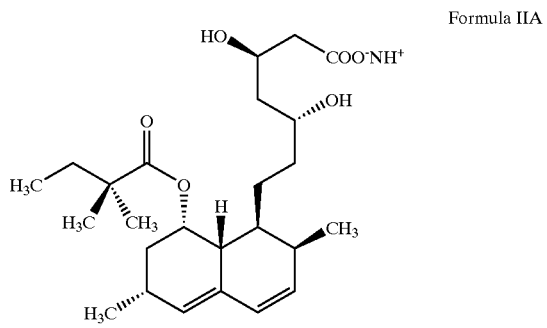

Formula IIA which is cyclized to obtain simvastatin and thus lactonization constitutes an essential step of the process. It is of considerable importance to employ an efficient method for the lactonization that can produce simvastatin of high purity in good yield.

The process disclosed in the U.S. Pat. No. 4,820,850 involves heating of hydroxyacid ammonium salt in toluene at 100° C. under a purge of nitrogen. The lactonization completion requires 6–8 hours refluxing and results information of increased amounts of dimer (Formula III).

Formula III

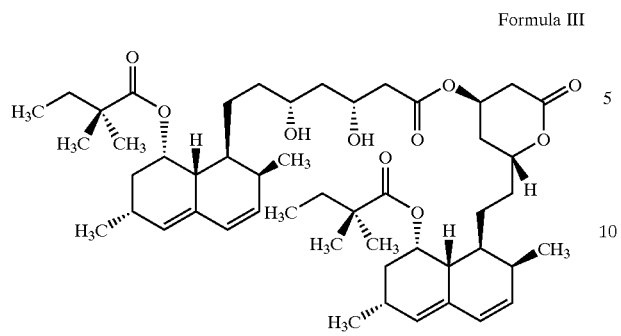

Formula II

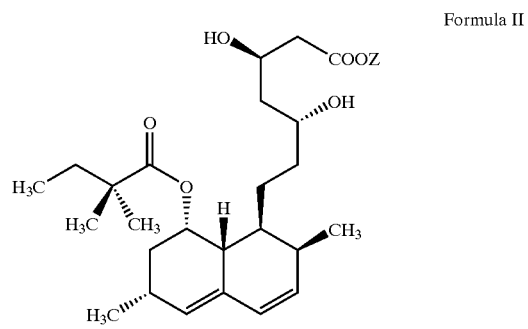

This dimer impurity is difficult to separate from the desired lactone even with repeated crystallization. The presence of dimer lowers the purity of the simvastatin product.

U.S. Pat. No. 4,916,239 describes another process where the lactonization reaction has been carried out by treating hydroxyacid ammonium salt in a mixture of acetic acid and water, and in the presence of a strong acid catalyst. This process requires gradual addition of water in several lots to effect crystallization of the lactonized product from the reaction medium to shift the equilibrium to the lactone side and this drives the lactonization to completion. This process is not amenable to industrial scale due to effluent generation and low purity of simvastatin product even though dimer content obtained is reported to be less than 0.2%.

U.S. Pat. No. 5,917,058 provides an alternate process to lactonize hydroxyacid or its salt by treatment with acetic acid under anhydrous conditions. The reaction is to be carried out essentially for a period of 5–7 hours and extensive water washing of the product is required to remove traces of acetic acid.

The aim of the present invention is to provide a highly efficient method for lactonization to produce simvastatin of greater than 99% purity in high yield. An example where simvastatin of greater than 99.5% purity has been achieved is cited in WO 99/42601 wherein the product was purified by successive crystallizations from aqueous acetone and from ethyl acetate.

BRIEF SUMMARY OF THE INVENTION

According to this invention, there is provided a process for lactonization to produce simvastatin, Formula I Formula I

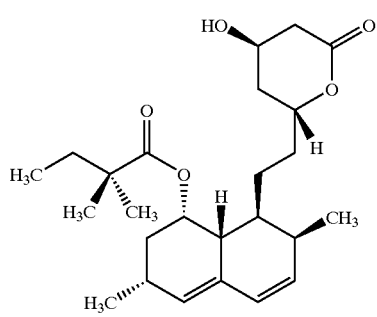

which comprises heating a compound namely acid or ammonium salt of compound of Formula II where Z is H or $NH_4$ in an organic solvent selected from xylenes, ethylbenzene and mixtures thereof at a temperature of 130 to 140° C.

The lactonization reaction (heating) is completed in 20–40 minutes.

The organic solvent is preferably xylenes and Z is $NH_4$.

DETAILED DESCRIPTION OF THE INVENTION

As an initial attempt, lactonization of hydroxyacid ammonium salt was carried out in toluene (Ref.: U.S. Pat. No. 4,820,850) and it was observed that dimeric impurity is formed to the extent of 0.6 to 1.0% and duration of reaction to attain starting material left unreacted to less than 2% by HPLC varied from 6 to 8 hours. Further, variation in results was observed depending upon the heating rate and flow of nitrogen purge. Examination of other lactonization procedures reported in literature concluded that cyclization in toluene yields reasonably pure simvastatin, the only disadvantage being the formation of excess dimer impurity. We reasoned that this impurity formation is due to longer reaction period in toluene and is not the result of higher reaction temperature of 100° C.

The instant invention relates to a novel process of lactonizing hydroxyacid ammonium salt in xylenes at reflux temperature. The lactonization reaction is efficiently accomplished within 30 minutes in presence of an antioxidant under a constant purge of nitrogen. The level of dimer impurity in the reaction mixture under the present cyclization conditions is restricted to less than 0.4% and isolation of the simvastatin lactone from the reaction mass reduces it further to less than 0.2% as recommended in Pharma Europa, Vol. 10, No. 3, September, 1998. This kind of smooth reaction and the product stability at high temperature were not anticipated and this observation constitutes an important part of the present invention.

The amount of xylenes is 20 to 50 parts by volume per part of the starting material, however, preferably 25 parts by volume is enough to carryout the lactonization reaction. The said reaction can be conducted in different solvents having boiling range above 110° C. such as ethylbenzene. The reaction is carried out at 110 to 140° C. but preferably at 130–140° C. Xylenes employed typically consist of about 98% orthoxylene, the remaining being meta- and para-xylenes. Further, an antioxident is added and nitrogen is bubbled through the reaction mass. Suitable antioxidants include butylated hydroxytoluene and butylated hydroxyanisole.

Product is isolated by distilling off xylenes and crystallization from cyclohexane to give simvastatin of greater than 99% purity. This can be further recrystallized from methanol and water to consistently attain more than 99.4% purity.

Typically, the lactonization reaction is conducted by heating simvastatin ammonium salt in xylenes at 135–140° C. for 30 minutes. However, it has been observed that extended heating in xylenes gives dimer to the extent of 0.65% against 1.2% in toluene.

The major advantages realized in the present lactonization conditions as compared to the prior art are increased process productivity and product purity. The reaction period is typically 30 minutes that demonstrates a greater efficiency. Xylenes are fully recovered and recycled in the process and no aqueous effluent is generated The following specific examples illustrate the process of this invention.

EXAMPLE 1

Preparation of (1S,3R,7S,8S,8aR)-3,7-Dimethyl-8-[2-[(2R,4R)-4-Hydroxy-6-OxO-3,4,5,6-Tetrahydro-2H-Pyran-2-YL]Ethyl]-1,2,3,7,8,8a-Hexahydro Naphthalin-1-Yl 2,2-Dimethylbutanoate Lactonization Ammonium 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoate (Formula II)(100 g, 0.220 mol) was added rapidly to xylenes (2500 ml) at 130–135° C. containing butylated hydroxytoluene (0.05 g) with nitrogen bubbling. Temperature of the reaction mixture was maintained at 135–138° C. for 30 minutes. Thereafter, it was cooled to 25–30° C. and treated carbon DC-enoanticromos (5 g) for 30 minutes. Suspension was filtered through celite and residue washed with xylenes (2×50 ml). Xylenes were removed at 60–65° C. under reduced pressure and the residue was dissolved in cyclohexane (2000 ml) at 80–85° C. The solution was cooled slowly with stirring to 10–15° C. and aged for 1 hour. The product was filtered and washed with cyclohexane (75 ml) and dried in vacuo to yield simvastatin (83 g, 90%) having HPLC purity 99.28%.

Crystallization from Methanol/Water

Simvastatin (83 g, 0.198 mol) was dissolved in methanol (830 ml) at 10–15° C. and DM water (830 ml) was added slowly over a period of 1 hour. The product slurry was cooled to 3–5° C. and was maintained at this temperature for 1 hour. The product was then filtered and washed with chilled methanol/water mixture (1:1 v/v, 50 ml) and dried in vacuo at 50–55° C. to obtain simvastatin (80 g, 96.4%) in pharmaceutically acceptable 99.55% HPLC purity. The level of dimer was <0.2% (0.18%).

EXAMPLE 2

Preparation of (1S,3R,7S,8S,8aR)-3,7-Dimethyl-8-[2-[(2R,4R)-4-Hydroxy-6-Oxo-3,4,5,6-Tetrahydro-2H-Pyran-2-Yl]Ethyl]-1,2,3,7,8,8a-Hexahydro naphthalin-1-Yl 2,2-Dimethylbutanoate Lactonization Ammonium 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoate (Formula II) (5 g, 11 mmol.) was added to xylenes (250 ml) and the reaction mass was refluxed at 138–140° C. with constant nitrogen purging. The reflux was continued for 30 minutes and reaction mass cooled to 25–30° C. HPLC reaction monitoring indicated unreacted ammonium salt (1.90%), simvastatin formation (94.8%) and dimer (0.24%). Xylenes were distilled off at 60–65° C. under reduced pressure. The residue was dissolved at 80–85° C. in cyclohexane (100 ml) and then cooled over 1 hour to 10–12° C. Product was filtered and washed with chilled cyclohexane (5 ml) and dried in vacuo at 45–50° C. to yield 4.2 g (91.4%) of the title compound with HPLC purity 98.9% and dimer content 0.15%.

Crystallization from Methanol/Water

This product was dissolved in methanol (42 ml) at room temperature and solution was cooled to 5–10° C. Water (42 ml) was added slowly in 30 minutes at 5–10° C. The product thus crystallized was stirred at 5–10° C. filtered and washed with cold methanol/water mixture (1:1 v/v, 8 ml). The product was dried to constant weight in vacuo at 45–50° C. to obtain simvastatin (4 g, 95.2%). Chromatographic purity (HPLC) 99.5% and dimer 0.16%.

EXAMPLE 3

Hydroxyacid ammonium salt of Formula II required in lactonization is prepared by the following procedure:

Step-I

Preparation of N-Benzyl-7-[1,2,6,7,8,8a(R)-Hexahydro-2(S),6(R)-Dimethyl-8(S)-[[2(S)-Methylbutanoyl]Oxy]-Naphthyl]-3(R),5(R)-Dihydroxy Heptanoic Acid Amide (Lovastatin Benzylamide)

A mixture of Lovastatin (50 g, 0.124 mol) and benzylamine (46.32 g, 0.432 mol) was mixed with toluene (25 ml) and heated to 80° C. under nitrogen atmosphere for 1 hour. Absence of Lovastatin was monitored by HPLC. Excess benzylamine and toluene were distilled off at 85–90° C. under reduced pressure (5–10 mm Hg). The residue was mixed with xylenes (50 ml) and distilled again at 85–90° C. under reduced pressure (5–10 mm Hg) to get product, lovastatin benzylamide, as light brown viscous liquid. Yield: 67.5 g.

Step-II

Preparation of N-Benzyl-7-[1,2,6,7,8,8a(R)-Hexahydro-2(S),6(R)-Dimethyl-8(S)-[[2(S)-Methylbutanoyl]Oxy]-Naphthyl]-3(R)-5(R)-Bis [(tert-Butyldimethylsilyl)Oxy]Heptanoic Acid Amide (Diprotected Lovastatin Benzylamide)

A solution of lovastatin benzylamide (63.26 g, 0.124 mol) in N,N-dimethylformamide (139 ml) was mixed with imidazole (21 g, 0.309 mol) and tert-butyldimethylsilyl chloride (51.42 g, 0.341 mol) at 25–30° C. under nitrogen atmosphere. Reaction mixture was heated to 60–65° C. and stirred for 4 hours. HPLC indicated complete conversion of lovastatin benzylamide into diprotected derivative.

Reaction mixture was cooled to 10–15° C. and methanol (2.85 ml) added and stirred for 30 minutes. Then the reaction mass was poured into a mixture of cyclohexane (1500 ml) and 5% aqueous sodium bicarbonate solution (750 ml) at 25–30° C. and stirred for 10 minutes. Layers were separated and organic layer was washed sequentially with 5% aqueous sodium bicarbonate solution (750 ml) and demineralized water (750 ml). The organic layer was concentrated completely at 55–60° C. under reduced pressure to obtain diprotected lovastatin benzylamide as viscous liquid. Yield: 99 g.

Step-III

Preparation of N-Benzyl-7-[1,2,6,7,8,8a(R)-Hexahydro-2(S),6(R)-Dimethyl-8(S)-[[2,2Dimethylbutanoyl]Oxy]-1(S)-Naphthyl]-3(R),5(R)-Bis[(tert-Butyldimethylsilyl)Oxy]Heptanoic Acid Amide (Diprotected Simvastatin Benzylamide)

A solution of pyrrolidine (25.1 g, 0.353 mol) in tetrahydrofuran (150 ml) was added slowly to a solution of n-butyllithium in hexanes (13.5%, 224 ml, 0.321 mol) at −25° C. to −20° C. over a period of 30 minutes. Reaction mixture was stirred for another 30 minutes at −25° C. to −20° C. The reaction mixture was then diluted with tetrahydrofuran (450 ml) and cooled to −50° C. Then added a solution of Step-II diprotected lovastatin benzylamide 91.4 g, 0.123 ml) in tetrahydrofuran (450 ml in 10 minutes while maintaining temperature below −40° C. The reaction mixture was stirred for 2 hours at −30° C. to −35° C. Methyl iodide (28.06 g, 0.197 ml) was added in one portion (exothermic reaction, temperature rises to −16° C.) and the reaction mixture was stirred at −30° C. for 1.5 hours. Progress of reaction was monitored by HPLC (starting material <0.1%). Temperature of reaction mixture was then slowly raised to −10° C. and stirred for 30 minutes. Reaction was then quenched by adding water (550 ml) and the contents were stirred for 10 minutes at 10° C. Layers were separated and organic layer was washed with 1N aqueous hydrochloric acid (550 ml) at 10° C. The organic layer was concentrated partially at 40–45° C. under reduced pressure to get crude product, diprotected simvastatin benzylamide, as brown liquid which is taken as such in the next step.

Step-IV

Preparation of Ammonium 7-[1,2,6,7,8,8a(R)-Hexahydro-2(S),6(R) Dimethyl-8(S)-[[2,2-Dimethylbutanoyl]OXY-1(S)-Naphthyl]-3(R),5(R)-Dihydroxyheptanoate (Simvastatin Ammonium Salt)

¹The above concentrated mass was dissolved in methanol (750 ml) at 25–30° and added methanesulphonic acid (2.22 g, 0.023 mol). The reaction mixture was stirred at 30–32° C. for 3 hours. Aqueous solution of sodium hydroxide (2N, 375 ml) was added and heated the reaction mixture to 78° C. A mixture of tetrahydrofuran and methanol (675 ml) was distilled out and afterwards the remaining reaction mixture was refluxed for 3 hours at 78–79° C.

Reaction mixture was then cooled to 60° C. and the solvents were removed in vacuo. The residue was diluted with water (25 ml) and cooled to 10° C. pH of the solution was adjusted to 7.0 by adding 3N hydrochloric acid (265 ml). Ethyl acetate (800 ml) was added and the pH was further lowered to 5.0 with aqueous hydrochloric acid. After stirring for 10 minutes at 15° C. layers were separated and aqueous layer was extracted with ethyl acetate (125 ml). Combined organic layers were diluted with methanol (250 ml) and warmed to 25–30° C. A mixture of aqueous ammonia (~25%) and methanol (1.3 v/v, 83 ml) was added slowly over a period of 30 minutes at 25–30° C. during which time product precipitates. Precipitated product was stirred at 25–30° C. for 30 minutes and cooled to −10° C. for 1 hour. Product was filtered and washed with a mixture of methanol and ethyl acetate (1.3 v/v, 50 ml) at 10° C. Product was finally dried under reduced pressure at 40–45° C. Yield: 40 g (HPLC purity >99%).

We claim:

1. A process for lactonization to produce simvastatin of Formula I

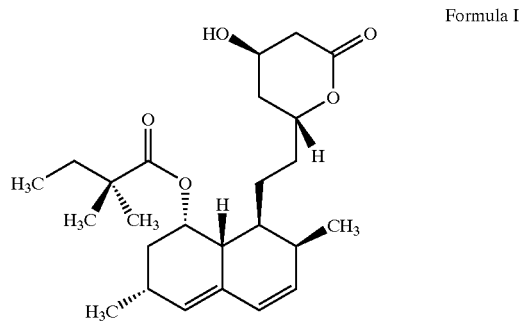

Formula I which comprises the steps of:

starting with a compound, namely acid or ammonium salt of compound of Formula II

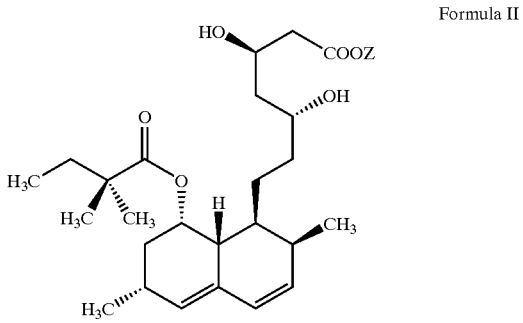

Formula II where Z is H or NH₄, cyclizing the said compound of Formula II in an organic solvent at a temperature greater than 110° C., distilling off all solvent to produce simvastatin of Formula I.

2. The process according to claim 1 where the said cyclization step is completed in less than 60 minutes.

3. The process according to claim 1 wherein organic solvent is xylenes.

4. The process according to claim 1 wherein Z in Formula II is NH₄.

5. The process of claim 1 where the said cyclization step is completed in 20–40 minutes.

6. The process of claim 1 where the said cyclization step is conducted reaction temperatures between 130° C.–140° C.

7. A process for lactonization to produce simvastatin of Formula I

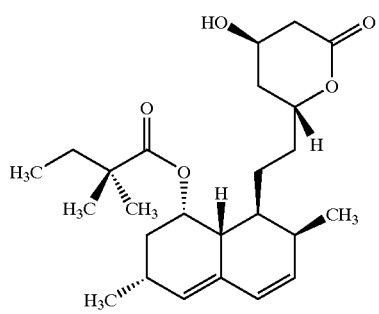

Formula I which comprises the steps of:

starting with a compound, namely acid or ammonium salt of compound of Formula II

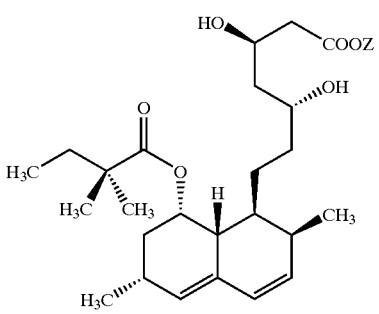

Formula II where Z is H or $NH_4$, cyclizing the said compound of Formula II in an organic solvent at a temperature greater than 110° C., distilling off all solvent to produce simvastatin of Formula I, crystallizing said simvastatin from a solvent or mixture of solvents to increase its purity.

8. The process as in claim 7 where the solvent or mixture of solvents used in the said crystallizing step is selected from the group consisting of methanol, water and cyclohexane.

* * * * *